United States Patent
Ding et al.

(10) Patent No.: US 8,315,428 B2
(45) Date of Patent: Nov. 20, 2012

(54) AUTOMATIC LINE IDENTIFICATION AND PAIRING FOR NUCLEAR IMAGING COLLIMATOR VECTOR MAP CHARACTERIZATION

(75) Inventors: Xinhong Ding, Buffalo Grove, IL (US); Ronald E. Malmin, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 257 days.

(21) Appl. No.: 12/909,963

(22) Filed: Oct. 22, 2010

(65) Prior Publication Data

US 2011/0096973 A1    Apr. 28, 2011

Related U.S. Application Data

(60) Provisional application No. 61/254,053, filed on Oct. 22, 2009.

(51) Int. Cl.
*G06K 9/00* (2006.01)
*A61B 6/00* (2006.01)

(52) U.S. Cl. ........................ 382/100; 382/274; 378/19

(58) Field of Classification Search .................. 382/100, 382/103, 106, 128, 129, 130, 131, 132, 133, 382/134, 162, 168, 173, 181, 232, 254, 274, 382/276, 305, 312; 378/4, 19, 21; 250/363.04, 250/505.1
See application file for complete search history.

(56) References Cited

U.S. PATENT DOCUMENTS

| | | | | |
|---|---|---|---|---|
| 4,958,081 A * | 9/1990 | Malmin et al. | ............. | 250/505.1 |
| 5,565,684 A * | 10/1996 | Gullberg et al. | ......... | 250/363.04 |
| 6,771,732 B2 * | 8/2004 | Xiao et al. | ........................ | 378/4 |
| 7,385,200 B2 * | 6/2008 | Vija | ......................... | 250/363.04 |
| 8,116,427 B2 * | 2/2012 | Kojima et al. | .................. | 378/19 |
| 2010/0054571 A1 * | 3/2010 | Kojima et al. | ................ | 382/131 |

* cited by examiner

*Primary Examiner* — Seyed Azarian
(74) *Attorney, Agent, or Firm* — Peter Kendall

(57) ABSTRACT

A method for measuring a SPECT collimator's hole orientation angles includes obtaining a set of stepped radiation line images of a line radiation source by scanning/stepping the line radiation source across a first collimator in a first direction; obtaining a second set of stepped radiation line images of the line radiation source across the first collimator in a second direction that is perpendicular to the first direction; and obtaining two sets of stepped radiation line images for a second collimator, wherein one of the two collimators is a reference collimator and the other is a collimator being measured. Calculating the collimator hole orientation angles requires determining offset distances along the two directions for each pair of lines between the reference collimator's line images and the measured collimator's line images by identifying and pairing the lines from the reference collimator line images and the measured collimator line images. The method provides an automated way of identifying and pairing the lines.

10 Claims, 8 Drawing Sheets

AUTOMATIC LINE IDENTIFICATION AND PAIRING FOR NUCLEAR IMAGING COLLIMATOR VECTOR MAP CHARACTERIZATION

CROSS-REFERENCE TO RELATED APPLICATION

This application claims the benefit under 35 U.S.C. §119(e) of U.S. Provisional Application Ser. No. 61/254,053, filed Oct. 22, 2009 the disclosure of which is incorporated herein by reference in its entirety.

FIELD OF THE DISCLOSURE

The disclosure generally relates to the field of nuclear image reconstruction, and more particularly, to a system and method for compensating for inaccuracies in collimator hole geometries to provide reduced distortion and improved resolution of tomographic images.

BACKGROUND

Single Photon Emission Computed Tomography (SPECT) reconstructs three dimensional images of radioactive source distributions in the body using a sequence of planar images acquired over a range of angles around the patient.

In order to reconstruct the tomographic image from the set of planar images it is necessary to know the direction from which the photons detected at a given point in the image originated. For X-ray computed tomography (CT), the direction is defined by a line from the anode to the X-ray detector. For Positron Emission Tomography (PET), it is a line between the pair of detectors in which the two coincident 511 keV photons are detected. In SPECT, the direction is usually defined by a collimator—a lead plate with 20,000 to 50,000 small holes formed in it which restricts the detected incident photons to only those with known angles of incidence at the detector.

The most popular collimator type is the parallel beam collimator, in which the holes are designed to point perpendicular to the detector surface. Another type of collimator is referred to as a fan beam collimator. With the fan beam collimator, the holes in one dimension (transverse) focus to a point; there is no focusing in the axial dimension. Another type of collimator is a cone beam collimator that focuses to a single point in both transverse and axial dimensions. Yet another type of collimator is a multi-focal or variable focal length fan beam collimators that has multiple focal points.

Image reconstruction algorithms in the current state of the art assume that the construction of these collimators is perfect. Such algorithms perform back projection of planar projection data and forward projections of the object estimates under this assumption. In reality, however, collimators are not perfect. Their construction is subject to dimensional errors such that all holes do not point in the ideal intended direction. This leads to errors in forward and backward projections and, results in distortions and degradation of the resolution in the final tomographic images.

More recently, a number of methods are being developed by those in the art to address the hole pointing errors of the collimators and account for the inaccuracies in the collimator hole pointing directions into the image reconstruction process to remove distortions and improve the image resolution. One of the methods that the inventors are aware of is a method in which the collimator holes' actual orientation or pointing directions are measured using a multiple parallel line radiation sources and incorporate that information into the image reconstruction process. The measurement method involves imaging a set of multiple parallel line radiation sources once through the collimator being measured and another time through a parallel hole reference collimator generating two sets of line images of the multiple line radiation sources. The lines in the line images represent the radiation intensity profiles of the radiation emitted by the multiple parallel line radiation sources. One set of the line images is associated with the collimator being measured and represents the intensity profiles of the radiation emitted by the multiple parallel line radiation sources collimated through the collimator being measured. The second set of the line images is associated with the reference collimator and represents the intensity profiles of the radiation emitted by the multiple parallel line radiation sources collimated through the reference collimator. Because of the geometries involved in the arrangement utilized in the method, the calculation of the collimator holes' orientation angles require pairing or matching of the lines in one set of line images to their corresponding lines in the second set of line images. An important aspect of the method is properly identifying and pairing the lines between the two sets of line images.

SUMMARY

According to an embodiment of the present disclosure, a method of efficiently conducting the pairing of the lines between the two sets of line images is disclosed. The method is part of an exemplary technique for mapping the hole directions over the entire surface of the collimator. The technique is applicable to arbitrary collimator geometries. A specific example is given for the multi focal collimator—a variable focal length fan in two independent dimensions—however, it will be appreciated that the system and method can be used with any collimator type.

According to an embodiment of the present disclosure, a method for measuring a SPECT collimator's hole orientation angles is disclosed. The method comprises: (a) providing a plurality of parallel spaced apart line radiation sources at a distance from a detector; (b) positioning a first collimator between the plurality of spaced apart line radiation sources and the detector; (c) obtaining a set of line images of the plurality of line radiation sources by scanning/stepping the plurality of line radiation sources across the first collimator in a first direction; (d) obtaining a second set of line images of the plurality of line radiation sources by scanning/stepping the plurality of line radiation sources across the first collimator in a second direction that is perpendicular to the first direction; (e) repeating the steps (c) and (d) for a second collimator, wherein one of the two collimators is a reference collimator and the other of the two collimators is a collimator being measured, whereby the line images obtained using the reference collimator are reference collimator line images and the line images obtained using the collimator being measured are measured collimator line images; (f) analyzing the reference collimator line images and the measured collimator line images and determining the offset distances dx, dy for each pair of lines between the reference collimator line images and the measured collimator line images; and (g) calculating hole orientation angles $\theta x$, $\theta y$ for each collimator hole in the collimator being measured. The step (f) comprises (h) identifying and labeling all peaks in the line profile data of the reference collimator line images and the measured collimator line images, based on each peak's position relative to a center of the field of view of the detector; (i) calculating peak statistics for each peak; (j) determining whether each peak is a valid peak that satisfies a predetermined condition based on the peak statistics and the position of each peak; (k) re-labeling each valid peak based on the position of the valid peak relative to the center of the field of view of the detector; and (l) pairing the valid peaks from the line profile data of the reference collimator line images with the corresponding valid peaks from the line profile data of the measured collimator line images according to the re-labeled position of the valid peaks.

According to another aspect, the present disclosure provides a method for reconstruction of single photon emission computed tomographic images wherein forward and/or backward projection procedures in the reconstruction utilizes actual measured SPECT collimator hole orientation angles, whereby the reconstructed tomographic images have improved image resolution.

BRIEF DESCRIPTION OF THE DRAWINGS

The details of the invention, both as to its structure and operation, may be obtained by a review of the accompanying drawings, in which like reference numerals refer to like parts, and in which.

DETAILED DESCRIPTION

Figure 1A:
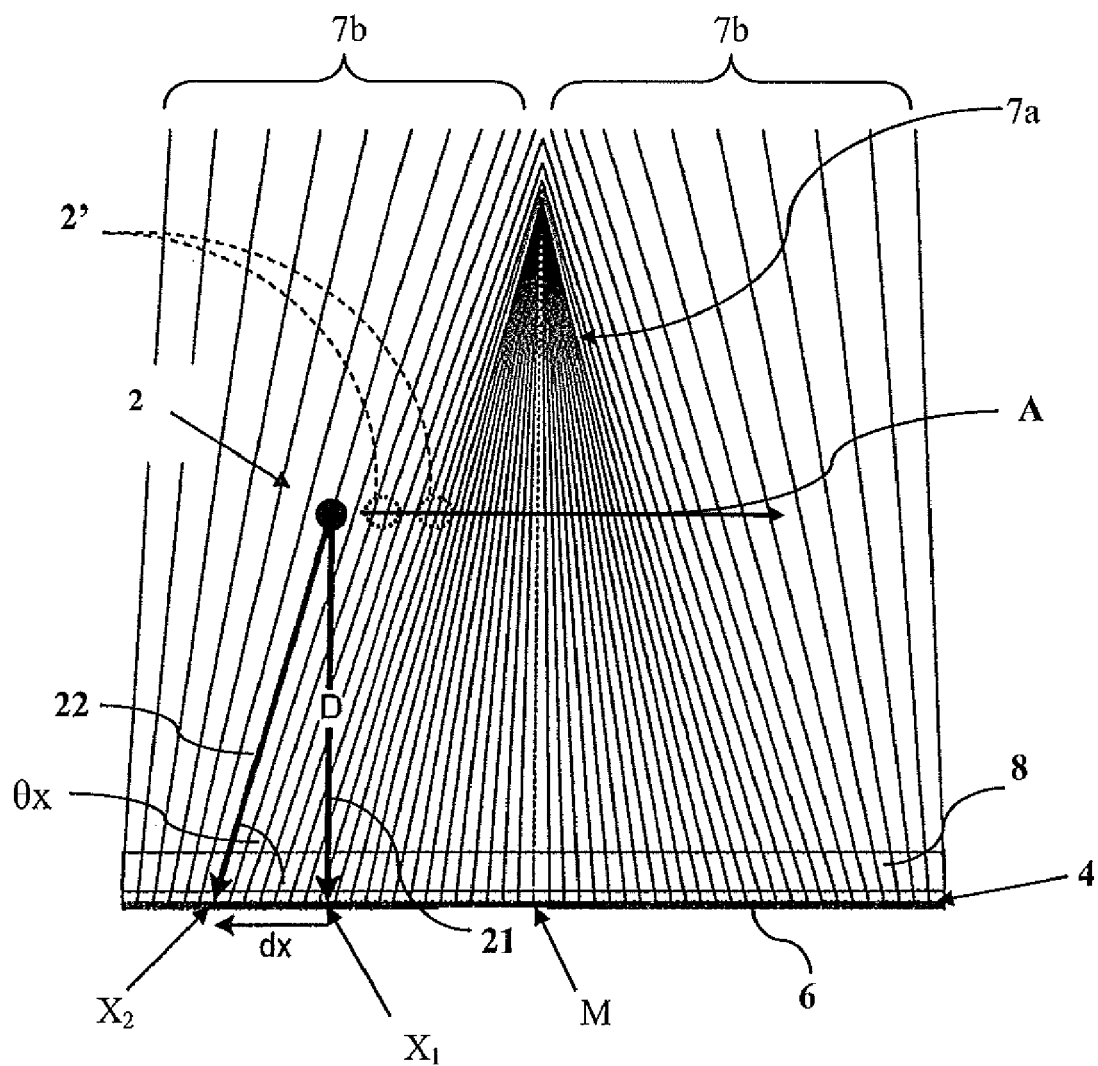
FIG. 1A shows a schematic representation of an arrangement for determining collimator hole angle using scanning radioactive line sources.

FIG. 1A shows a schematic of an arrangement 10 for use in measuring the hole orientation angles of a collimator 8. The arrangement 10 allows measuring the collimator hole angles using one or more line radiation sources 2. The measured collimator hole angles are then compiled into a vector map providing the orientation of the holes in the collimator 8 that can be incorporated into the forward and/or backward projection steps of tomographic reconstruction in SPECT imaging. Knowing the actual orientation of the collimator holes rather than assuming that they are oriented in the intended ideal orientation makes the forward and backward projection process more accurate.

The method of measuring the orientation of the collimator holes will now be described in conjunction with the FIGS. 1A-5, Referring to FIG. 1A, a line radiation source 2 is positioned at a known distance D above the interaction plane 4 of a medical imaging detector 6. A collimator 8, whose hole angles are to be measured, e.g. a multi-focal length collimator, is positioned between the line radiation source 2 and the detector 6. The line radiation source 2 is configured and adapted to be controllably movable or scanned in a direction A parallel to the interaction plane 4 of the detector 6 so that the line radiation source 2 maintains its distance D above the detector's interaction plane 4.

Figure 2:
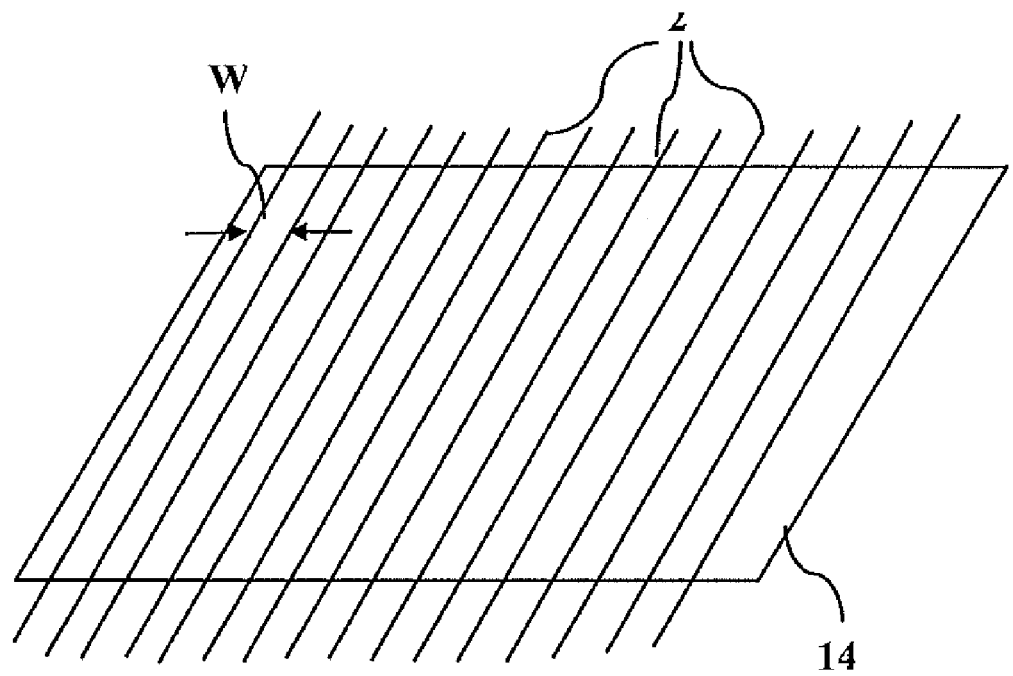
FIG. 2 is a schematic illustration of an example of a plurality of parallel line radiation sources.

FIG. 1A shows only one line radiation source 2 viewed from one end of the line radiation source 2 for purpose of simplifying the description. In practical application, however, for matter of efficiency, a plurality of parallel line radiation sources are used to cover the whole field of view of the detector 6 in order to minimize the time required to make the measurements. For example, FIG. 2 shows a carrier 14 on which is provided a plurality of the line radiation sources 2. The plurality of line radiation sources 2 are in parallel arrangement and they are a set distance W apart. The absolute value of the spacing distance W is arbitrary but it is a fixed value for a given set of line radiation sources 2. The line radiation sources 2 are filled with an appropriate isotope. In one embodiment, a total of twenty line radiation sources filled with technetium isotope are used. It will be appreciated that other isotopes, and a greater or lesser number of line sources may also be used.

Figure 1B:
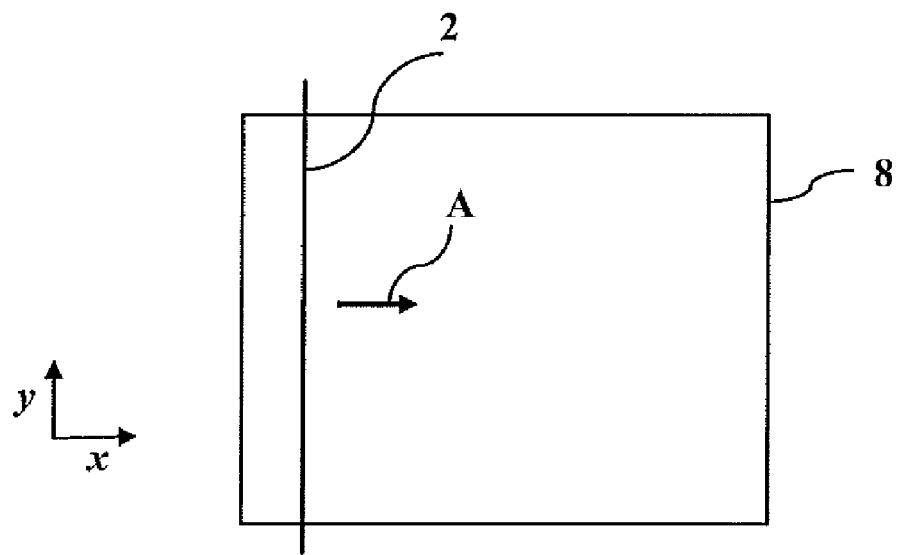
FIG. 1B shows a top-down schematic view of a collimator and a scanning radioactive line source illustrating the orientation and scanning direction of the line source with respect to the collimator.

FIG. 1B shows a schematic top-down view of the arrangement 10 showing a line radiation source 2 above the collimator 8. The collimator 8 is a 2-dimensional array of holes that extend in parallel rows in the x and y directions noted in the drawing. The holes' locations are defined in an x-y coordinate as shown and the line radiation source 2 is configured to be parallel to one of the x or y axes of the collimator 8 and movable in direction A that is perpendicular to the line radiation source. In the illustrated example, the line radiation source 2 is parallel to the y axis and is being scanned along the direction A which is orthogonal to the y axis and parallel to the x axis. Thus, the view shown in FIG. 1A shows the arrangement 10 along the x axis.

Using the illustration of FIG. 1A, measuring the orientation angle of one hole in the collimator 8 along the x axis will be described. The measurement of the hole angles or orientation would mostly be necessary for fan beam collimators or variable focal length fan beam collimators whose holes are oriented at angles other than orthogonal to the collimator surface to one or more focal points. In the illustrated example, the collimator 8 is a variable focal length fan beam collimator as represented by the hole orientation lines 7. The holes of the collimator 8 are configured to form a fanbeam region 7a and variable focal length regions 7b.

First, an image of the line radiation source 2 is taken using the detector 6 through the variable focal length fan beam collimator 8. The detector will see the line radiation source 2 through rows of detector pixels located near $X_2$ on the detector 6 which have a direct line of sight to the line radiation source 2 through the collimator 8. By this, we mean that the rows of detector pixels detects the radiation beam 22 from the line radiation source 2 through a particular row of collimator holes that is aligned between the line radiation source 2 and the rows of detector pixels near the position $X_2$. We referred to rows of detector pixels near the position $X_2$ rather than a single row of detector pixels because the detector pixels are much smaller than the collimator holes and the radiation collimated by the collimator holes and impinging on the detector 6 would energize more than one row of detector pixels near the position $X_2$. It should be noted that other than the row of collimator holes along the midline M of the variable focal length fan beam collimator 8, the holes are oriented at some angle θx. Thus, the image of the line radiation source 2 is detected by the detector pixels near position $X_2$ that are displaced by a distance dx from a reference position $X_1$ that is directly under the line radiation source 2. The position $X_2$ will be referred to herein as the measured position.

Next, another image of the line radiation source 2 is taken using the detector 6 through a parallel hole reference collimator (not shown). Because the holes in the parallel hole reference collimator are oriented orthogonal to the plane of the collimator, the detector will see the line radiation source 2 through the rows of detector pixels located near the reference position $X_1$ by detecting the radiation beams traveling along the line 21 and impinging on the detector pixels. Thus, by comparing the two line images, the offset distance dx between the reference position $X_1$ and the measured position $X_2$ can be measured.

Because the line radiation source 2 is always at a distance D from the detector's surface 4, the row of the detector pixels at the reference position $X_1$ are at a distance D from the line radiation source 2, and we see that the line radiation source 2, $X_1$ and $X_2$ form a right triangle. And because D and dx are known, the angle θx is related to D by tan θx=dx/D and θx can be calculated using the formula:

$$\theta x = \tan^{-1}(dx/D) \qquad (1)$$

One would readily understand that the order in which the two line images are taken is not important. In other words, the line image for the reference collimator can be taken first or after the line image for the collimator 8 being measured. By repeating the steps described above along the y axis of the collimator 8, the angular orientation of the collimator hole in the y direction can be measured.

One can readily understand that the accuracy of the measured hole angle θx is dependent upon the accuracy of the collimator holes in the parallel hole reference collimator. However, the parallel hole collimators, whose holes are all aimed orthogonal to the collimator surface, tend to have much better dimensional accuracy and the holes are aimed true to their intended direction and the inventors have found that they do not substantially affect the accuracy of the measured hole angle θx. In one embodiment, the parallel hole reference collimator would have a dimensional tolerance of less than ±0.1 mm.

In order to measure the orientation angle of all of the collimator holes along the x axis, one can capture images of the line radiation source 2 through all of the collimator holes along the x axis by scanning the line radiation source 2 in multiple steps across the width of the collimator 8 along the x axis and take images at each stepped position 2'. This would need to be performed once with the parallel hole reference collimator and once with the collimator 8 being measured. However, because a collimator generally has hundreds of holes across its width, this process can take a long time using one line radiation source.

Thus, in a practical application of the method, a plurality of line radiation sources as shown in FIG. 2 can be used. FIG. 2 shows a carrier 14 holding a set of a plurality of line radiation sources 2 positioned in parallel relation and separated by a fixed distance W. According to a preferred embodiment, the line radiation sources 2 are provided in sufficient number to cover the width of the collimator 8. For purpose of discussion, we use an example where 20 line radiation sources that are spaced 2 cm apart on the carrier 14 sufficiently spans the width of the collimator 8. In this embodiment, the carrier 14 is scanned across the width of the collimator 8 in 2 mm stepped increments. At 2 mm increments, a total of ten discrete steps are all that is necessary to scan the whole width of the collimator 8.

At each stepped position, an image of the plurality of line radiation sources 2 is taken using the detector 6 similar to the single line radiation source example discussed above in connection with FIG. 1A. Thus, a set of images of the line radiation sources 2 are produced corresponding to each stepped position. These images will be referred to herein as "line images." At each discrete stepped position of the plurality of line sources 2 during this scanning/stepping, the mechanical position (in the x-y coordinate of the collimator 8) of the line sources 2 and the line images obtained by the detector 6 are stored in a suitable storage medium provided in the controller system that is carrying out the scanning. Similar to the single line radiation source example, the scanning/stepping procedure producing the set of line images is performed once with a parallel hole reference collimator and another time with the collimator 8 being measured. The two scanning/stepping procedures, one with the reference collimator and the other with the collimator being measured, are carried out so that the mechanical positions for the plurality of line radiation sources 2 at each of the stepped interval are same in both scanning/stepping procedures.

Figure 3A:
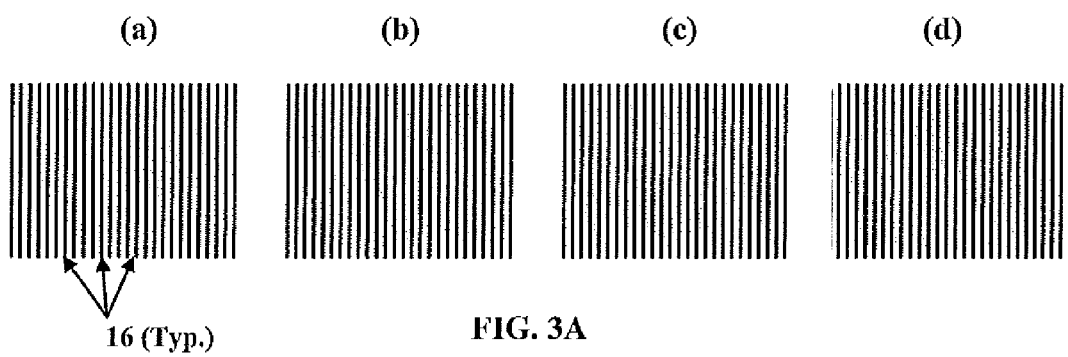
FIG. 3A is a set of line images generated by imaging the plurality of parallel line radiation sources through a parallel hole reference collimator.
Figure 3B:
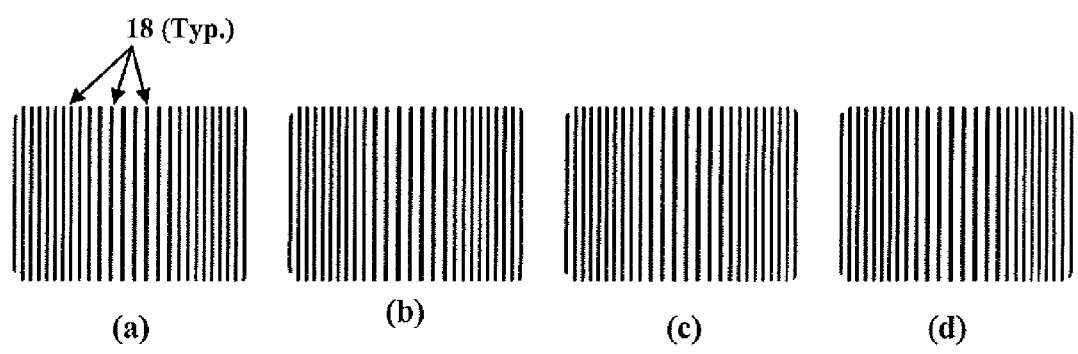
FIG. 3B is a set of line images generated by imaging the plurality of parallel line radiation sources through a collimator being measured, a variable focal length fan beam collimator.

The scanning/stepping performed with the parallel hole reference collimator generates a set of line images representing a series of the reference positions $X_1$. The scanning/stepping performed with the collimator 8 generates a set of line images representing a series of the measured positions $X_2$. FIG. 3A shows an example of the series of line images 16 representing a series of the reference positions $X_1$. FIG. 3B shows an example of the series of line images 18 representing a series of the measured positions $X_2$. In other words, FIG. 3A is a series of images of the intensities of collimated radiation impinging on the detector 6 for the parallel hole reference collimator, while FIG. 3B is the corresponding series of images of the intensities of collimated radiation impinging on the detector 6 for the variable focal length fan collimator 8. The line images (a)-(d) in both sets of images represent the images taken at first four of the ten stepped intervals. In this embodiment, going from left-to-right, the entire carrier 14 holding the plurality of line radiation sources is translated by two millimeters per step, such that, after ten steps the collimator 8 has been sampled in two millimeter increments in the x axis direction.

The distance dx is obtained by noting the difference in the positions of respective lines in the two series of images. However, because each line in the line images are produced by multiple rows of detector pixels, each line is a raw image of ~10-15 pixels wide (along x axis) having approximately gaussian profile along the x axis direction. Therefore, the position of the lines ($X_1$ and $X_2$) along the x axis direction at a given detector pixel position in the y axis direction must be determined by finding the "center" of the imaged line's intensity profile in the x direction ("x-profile"). At each line's y axis position (along the y-dimension or vertical in the images of FIGS. 3A and 3B), the center of the imaged line's x-profile can be determined by standard peak locating techniques.

These include fitting a gaussian curve to the line's x-profile and calculating the centroid of the line's x-profile, or other peak location metrics.

After the dx values for each of the line images in FIGS. 3A and 3B are calculated, the collimator hole angles θx along the x axis direction can be calculated using the equation (1) discussed above. It would be obvious to one or ordinary skill in the art that the collimator hole angles θy along the y axis direction for the variable focal length fan beam collimator 8 can be calculated by repeating the scanning/stepping process described above in the y axis direction using the parallel hole reference collimator and the variable focal length fan beam collimator 8. That process would generate another set of series of line images similar to those shown in FIGS. 3A and 3B, from which dy values (analogous to dx values) can be calculated and then the orientation angles θy along the y axis direction can be calculated using the formula:

$$\theta y = \tan^{-1}(dy/D).$$

The scanning/stepping process for the y axis direction would be carried out by rotating the carrier 14 by 90 degrees so that the plurality of line radiation sources 2 are now oriented orthogonal to the orientation shown in FIG. 1B. This will allow the plurality of line radiation sources 2 to be scanned/stepped across the collimator 8 along its width in the y axis direction. (See FIG. 1B for the x-y axis orientation).

Figure 5:
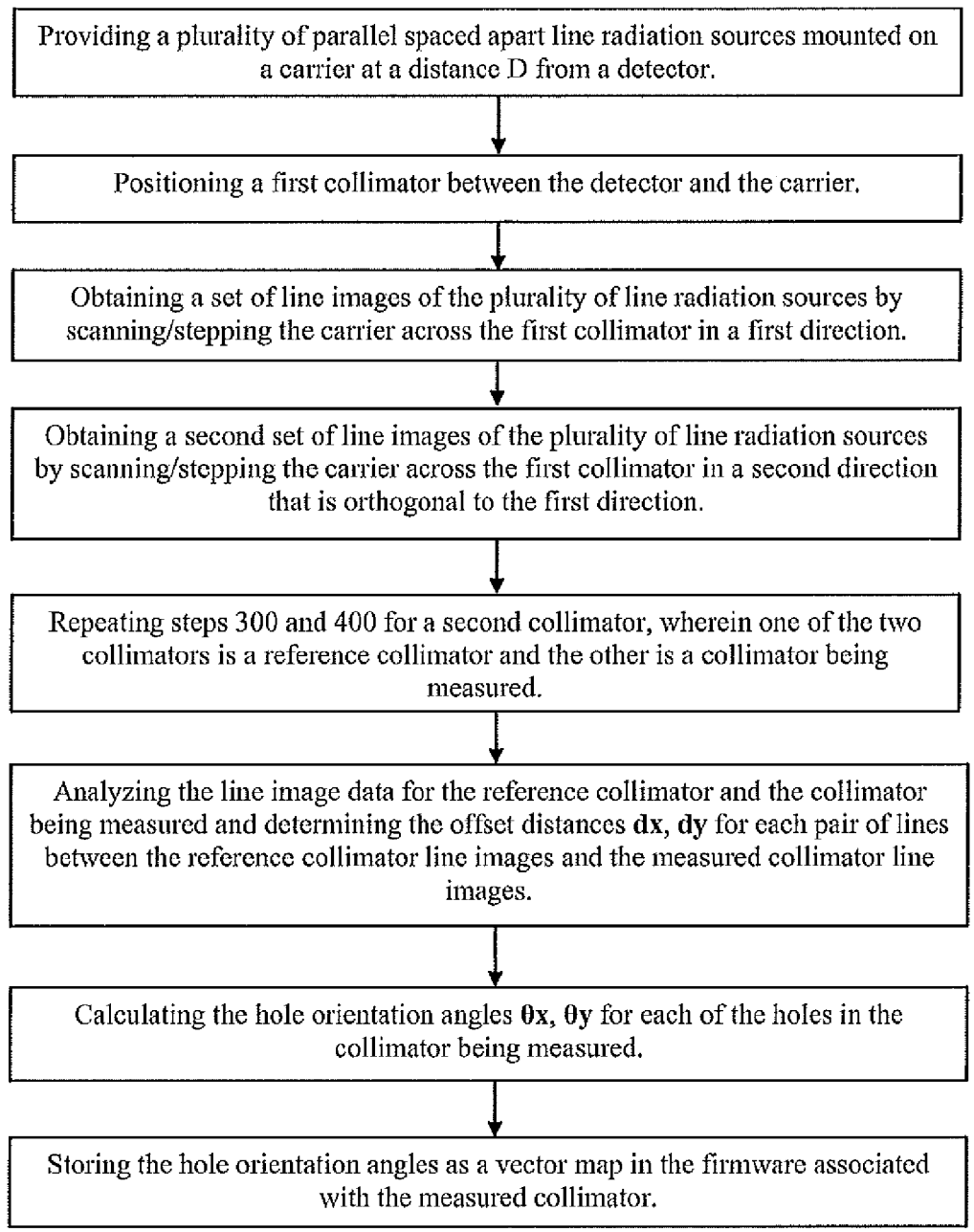
FIG. 5 is a flowchart describing a method of determining collimator hole angle according to an aspect of the present disclosure.

The offset distance dx data from x-axis scan and dy from the y-axis scan are combined to generate a data set, vector map, of the collimator holes in the collimator 8. The vector map would include the θx and θy values for each hole of the collimator 8. The vector map is stored as part of the firmware associated with the particular collimator 8 so that a particular SPECT system in which the collimator 8 is installed, the SPECT system would be able to utilize the collimator's vector map data to accurately perform forward and/or back projection in reconstructing the SPECT image. FIG. 5 shows a flowchart summary of the overall method of determining collimator hole angle just described.

The calculation of the offset distances dx and dy discussed above requires identifying a pair of lines whose positions mark $X_1$ and $X_2$. This requires comparing a pair of line images, one taken with the reference collimator and the other taken with the collimator being measured, from the same scanning/stepping position, and matching up or pairing the lines in one line image to the lines in the other line image. Because each of the lines correspond to a different line radiation source among the plurality of line radiation sources mounted on the carrier 14, two lines that correspond to the same line radiation source must be paired together to correctly calculate dx, dy and, in turn, θx, θy. The present disclosure provides a method of performing this pairing of the lines from the line images in an efficient manner.

Figure 4A:
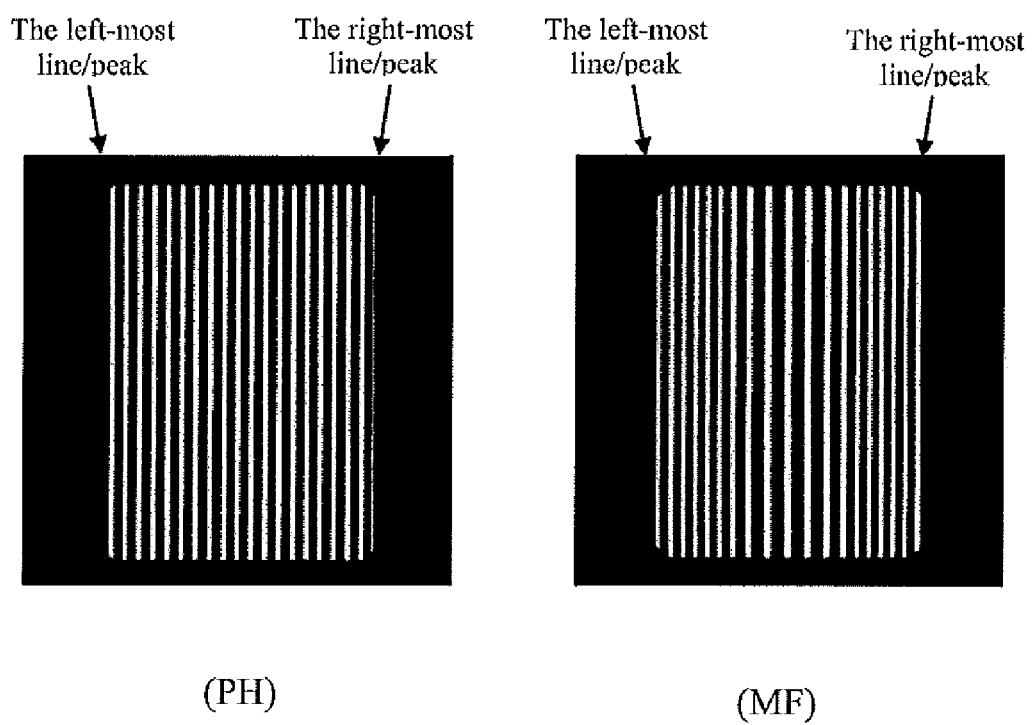
FIG. 4A shows a pair of line images from one particular scanning/stepping position, one from the set of line images generated with the parallel hole reference collimator and the other generated with the variable focal length fan beam collimator.

In order to illustrate the method, we refer to FIG. 4A, showing a pair of line images, labeled as (PH) and (MF), from one particular scanning/stepping position. (PH) is one line image from the set of line images generated with the parallel hole reference collimator and (MF) is one line image from the set of line images generated with the variable focal length fan beam collimator 8. Because of the movement of the carrier 14 relative to the detector 6 and its field of view (FOV) during the scanning/stepping procedure the left-most line or the right-most line may not represent a valid line because the view of the line radiation source may not have been fully captured because of the edge of the detector's FOV. Thus, the method of the present disclosure will (1) first identify the first valid line and the last valid line; and (2) for each valid line from the (MF) image determine the corresponding valid line from the (PH) image, and do this for each pair of (PH), (MF) images at each scanning/stepping position.

Figure 4B:
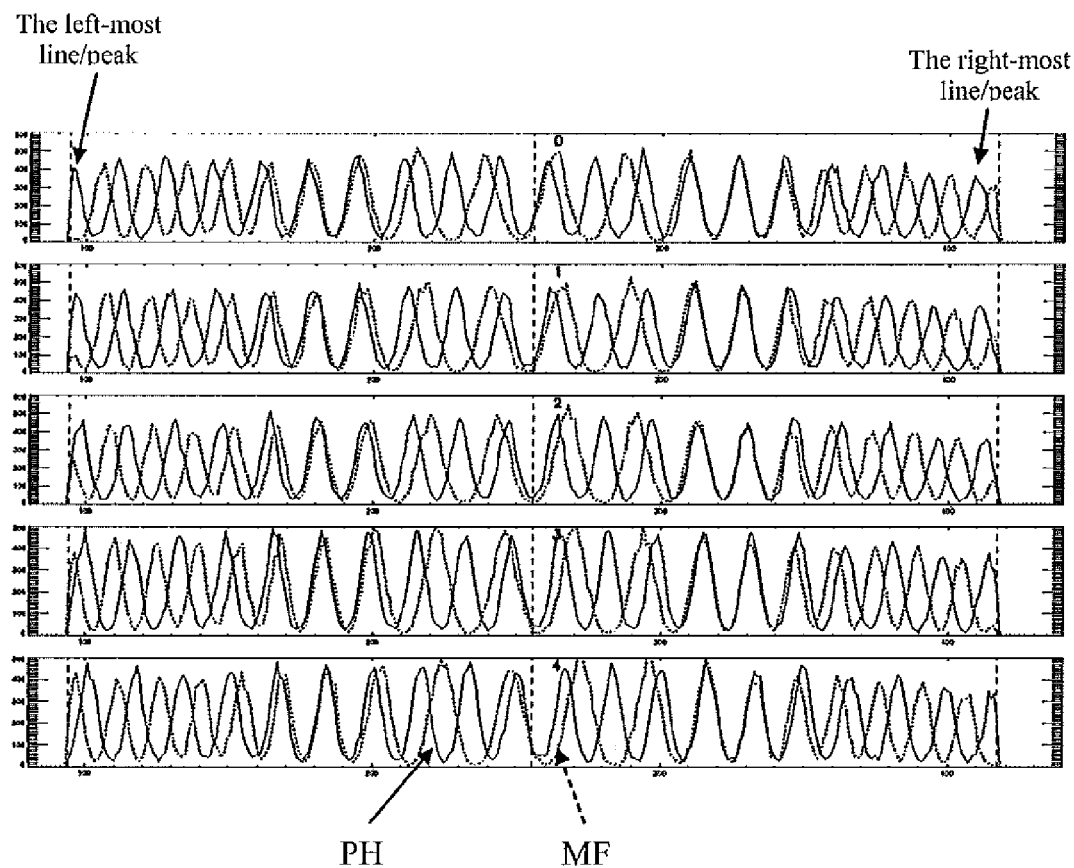
FIG. 4B shows a radiation intensity profile plot representing a line image data.

As described above, the line images are graphical illustrations of the radiation intensities of the radiation from the plurality of line radiation sources 2 impinging on the detector 6. Therefore, the image data for each of the line images that are stored and processed by the illustrative system 50 (see FIG. 6) are radiation intensity profiles as shown in FIG. 4B. FIG. 4B shows five pairs of line profiles (i.e. radiation intensity profiles) representing five scanning/stepping positions. Each pair of curves correspond to the line profiles at a particular scanning/stepping position. At each position, the two curves represent the line profiles from the (PH) image and the (MF) image and the peaks in the curves represent the line radiation sources that produced the lines in the line images. The procedure for identifying the valid lines and paring the valid lines from the (PH) image data to the corresponding valid lines from the (MF) image data uses these line profile data by identifying the peaks in the curves.

Figure 6:
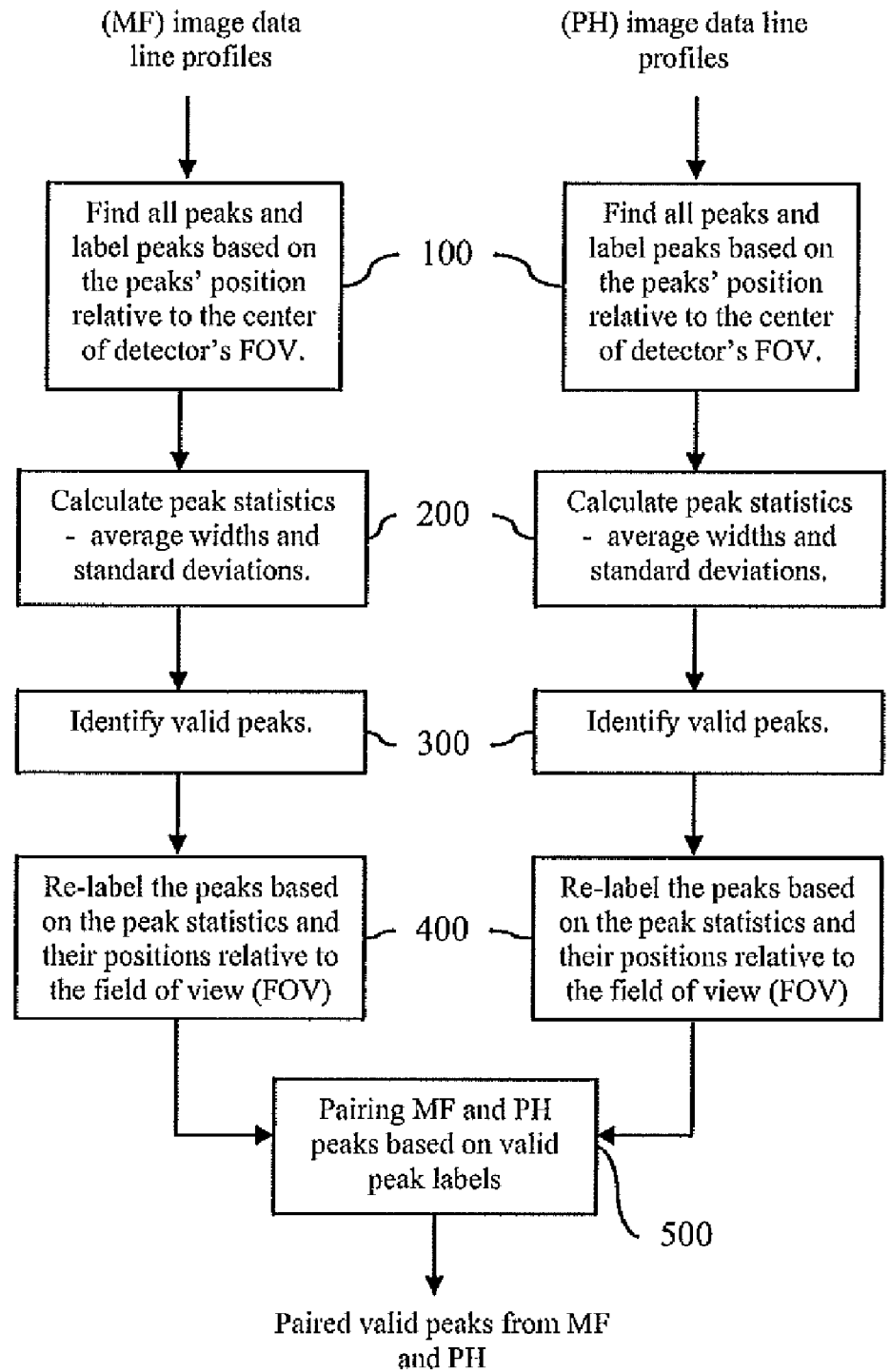
FIG. 6 is a flowchart describing the automatic line association method for pairing the radiation intensity profile lines between the set of line images for a reference collimator and another set of line images for a collimator being measured according to an embodiment of the present disclosure.

FIG. 6 shows a flow chart that illustrates the main steps of the valid line identification and line pairing process. First, all peaks are identified and labeled in the line profiles of each of the (PH) and (MF) image data. (See box 100). Each peak is labeled based on the peak's distance from the center of the detector's FOV. Because the peaks are labeled based on their distance from the center of the line image, the peaks in a given line image data for a particular scanning/stepping position have ordered labels represented by a set of integers:

$$-L_x, -L_x+1, \ldots, -2, -1, 1, 2, \ldots, R_k-1, R_k,$$

where $R_k$ denotes the label of the right-most peak at kth scanning/stepping position, $-L_k$ denotes the label of the left-most peak at kth scanning/stepping position, and k runs from 1 to n, where n is the total number of scanning/stepping positions. In the illustrated example, the plurality of line radiation sources 2 are 2 cm apart and the scanning/stepping steps are 2 mm, so n=10.

In order to determine if a peak is valid or not, a set of statistics, the average width and standard deviation of the peak, are calculated for each peak. (See box 200). This step involves first finding the maximum common label L and the minimum common label R across all scanning/stepping positions, $$L = \max(L_1, L_2, \ldots, L_{10}), R = \min(R_1, R_2, \ldots, R_{10})$$

followed by computing the mean width $\mu_w$ and the standard deviation $\sigma_w$ for peaks with label L+1 or R−1, where $\mu_w$=average width of peaks across all scanning/stepping positions with labels L+1 or R−1, and $\sigma_w$=the corresponding standard deviation.

Based on the statistics $\mu_w$ and $\sigma_w$, together with the peak distance relative to the FOV of the detector, the valid peaks are now identified. (See box 300). The valid peaks are identified using the following criteria. Let P=(x, w) denote an arbitrary peak, where x is the peak position measured in millimeters relative to the left side of the given line image and w is the peak width. The position of the peak is referenced from the left side of the line image because the scanning/stepping is conducted from left to right and the (0, 0) coordinate of the pixels in the detector 6 is the upper right hand corner of the image. P is a valid peak if the following two predetermined conditions are satisfied:

1) $x > x_{min} + \alpha \mu_w$ and $x < x_{max} - \alpha \mu_w$, where $[x_{min}, x_{max}]$ is the FOV interval and α is a predetermined threshold value 0.6, for example;
2) $|w - \mu_w| < \beta \sigma_w$, where β is another predetermined threshold value 2, for example).

The predetermined condition 1) verifies whether the peak is within the detector's FOV and as long as α>0.5, the predetermined condition 1) implies that the peak is within the FOV, so 0.6 is selected to provide a little bit More space from the edge of the FOV. In the predetermined condition 2), β refers to how many deviations away w is from the $\mu_w$. 2 or 3 deviations away usually considered quite large and thus the value of 2 is selected. Next, the valid peaks are re-labeled based on the peak statistics and their positions relative to the FOV. (See box 400). Finally, the re-labeled valid peaks from the (MF) image data are paired with the corresponding valid peaks from the (PH) image data. (See box 500). Consistent with the discussions provided above, the positions of the valid peaks in the (PH) image data represent the reference positions $X_1$ for each line and the positions of the valid peaks in the (MF) image data represent the measured positions $X_2$ for each line and the dx, dy and θx, θy can be calculated. The hole orientation angles θx, θy can be stored as a vector map in the firmware associated with the measured collimator for use by the SPECT system in which the collimator is ultimately installed.

Figure 7:
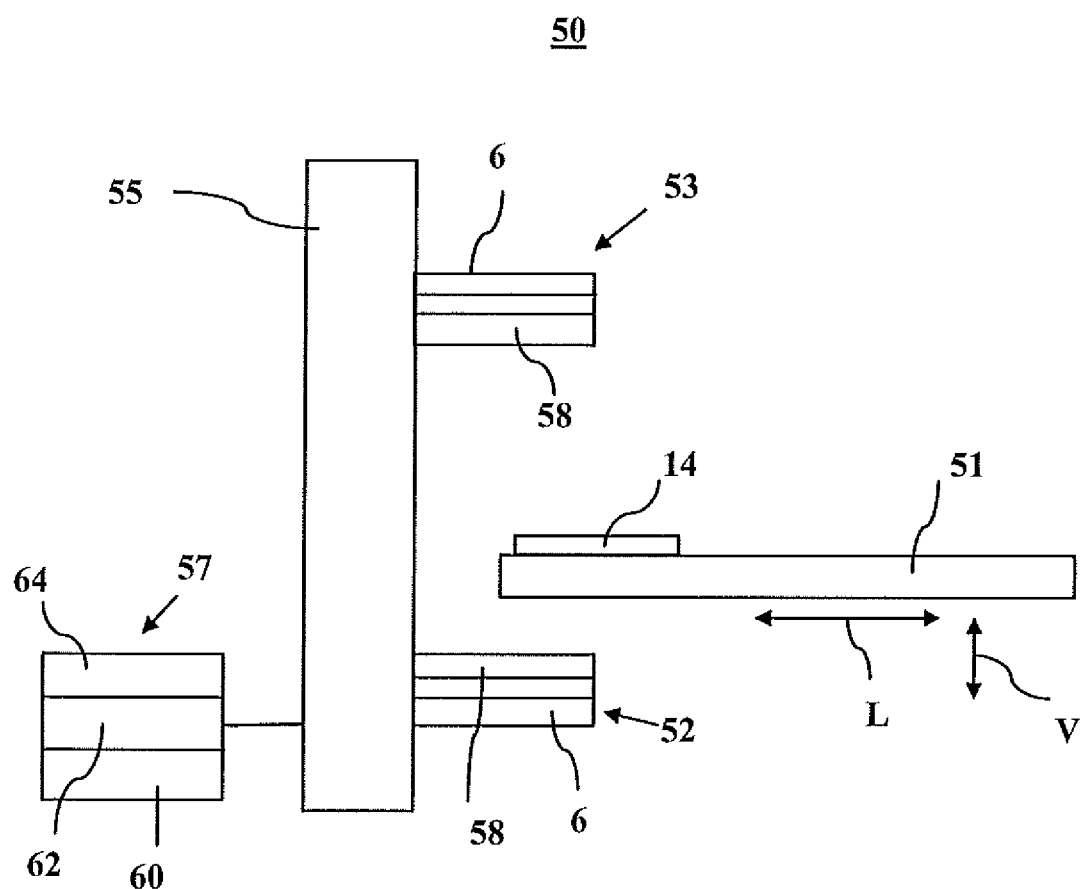
FIG. 7 shows a schematic illustration of a SPECT system that can be used to perform the method of the present disclosure.

FIG. 7 is an example of a system 50 that can be utilized to implement the arrangement 10 of FIG. 1A. In this example, the system 50 is a SPECT system comprising at least a patient bed 51, detector units 52, 53, a gantry 55 providing support for the detector units 52, 53 and a control unit 57. The patient bed 51 is configured and adapted to be controllably movable in lateral directions L, as well as vertical direction V. The patient bed 51 is used to hold the patient during the normal operation of the SPECT system, however, in this embodiment, the SPECT system 50 is utilized for the method described herein and the patient bed 51 is utilized as the movable stage on which the carrier 14 is mounted for performing the scanning/stepping procedure. The lateral movement of the patient bed 51 in the direction L includes the directions along the x or y axes in the collimator's x-y coordinate plane, as well as vertical direction V. The detector units 52, 53 each generally comprise a collimator 58 and a detector 6. The operation of the system 50 and the movement of the patient bed and the detector units 52, 53 are controlled by the control unit 57. The control unit 57 is provided with appropriate processor units 60, machine-readable memory units 62, and user interface units 64 for proper functioning of the system 50.

According to one embodiment, the arrangement 10 of FIG. 1A can be implemented on the SPECT system 50 by mounting the array 14 to the patient bed 51. The parallel hole collimator and the collimator 8 to be measured are positioned in place of the collimator 58 of either the detector unit 52 or 53. The motion of the movable patient bed 51 in a SPECT system 50 can be accurately controlled and thus can be used for the scanning/stepping process by moving the array 14 in stepped increments over the detector unit 52, for example, while maintaining the distance between the array 14 and the interaction plane 4 of the detector 6 to the fixed distance D. The data collected by the detector 6 would be processed and stored in the control unit 57 so that the processor units 60 can carry out the methods described above for calculating the dx, θx and dy, θy including the procedures for identifying and pairing the valid lines between the (PH) line image data from the reference collimator and the (MF) line image dat from the measured collimator. The series of line images such as those shown in FIGS. 3A, 3B would be generated by the processor units 60 and stored in machine-readable memory units 62.

Accuracy of the system can be increased by an iterative process whereby the pixel location in the direction orthogonal to the focusing direction is re-computed using the map of the orthogonal direction angles. Details of such second order processes will vary with type of focusing collimation, but are obvious to those skilled in the art.

As noted, the embodiments described herein utilized a variable focal length fan beam collimator 8 as an example but, it will be appreciated that the disclosed system and method can be used to measure the hole angles of a variety of collimator types.

It will be appreciated that although the disclosed embodiments describe scanning/stepping the plurality of line radiation sources 2 with respect to the collimator and detector 6, it is contemplated that the line sources 2 can instead be held stationary and the collimator and detector 6 can be moved in stepped increments. The important point is that the line radiation sources 2 and the collimator and the detector 6 can be controllably stepped across with respect to each other to generate the series of line images from the collimated radiation impinging on the detector 6.

The method for operating the disclosed arrangement, as described herein, may be automated by, for example, tangibly embodying a program of instructions upon a machine-readable storage media, such as the machine-readable storage unit 62 of the SPECT system 50, capable of being read by a machine, such as the processor unit 60, capable of executing the instructions. A general purpose computer and/or computer processor is one example of such a machine. A non-limiting exemplary list of appropriate storage media well known in the art would include such devices as a readable or writeable CD, flash memory chips (e.g., thumb drives), various magnetic storage media, and the like.

The features of the system and method have been disclosed, and further variations will be apparent to persons skilled in the art. All such variations are considered to be within the scope of the appended claims. Reference should be made to the appended claims, rather than the foregoing specification, as indicating the true scope of the disclosed method.

The functions and process steps disclosed herein may be performed automatically or wholly or partially in response to user command. An activity (including a step) performed automatically is performed in response to executable instruction or device operation without user direct initiation of the activity.

The disclosed systems and processes are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The processes and applications may, in alternative embodiments, be located on one or more (e.g., distributed) processing devices accessing a network linking the elements of the disclosed system Further, any of the functions and steps provided in FIG. 5 may be implemented in hardware, software or a combination of both and may reside on one or more processing devices located at any location of a network linking the elements the disclosed system or another linked network, including the Internet.

Thus, although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A method for measuring a single photon emission computed tomography collimator's hole orientations, comprising:
   (a) providing a plurality of parallel spaced apart line radiation sources at a distance from a detector, the detector having a field of view;
   (b) positioning a first collimator between the plurality of spaced apart line radiation sources and the detector;
   (c) obtaining a set of line images of the plurality of line radiation sources by scanning/stepping the plurality of line radiation sources across the first collimator in a first direction;
   (d) obtaining a second set of line images of the plurality of line radiation sources by scanning/stepping the plurality of line radiation sources across the first collimator in a second direction that is orthogonal to the first direction;
   (e) repeating the steps (c) and (d) for a second collimator, wherein one of the two collimators is a reference collimator and the other of the two collimators is a collimator being measured, whereby the line images obtained using the reference collimator are reference collimator line images and the line images obtained using the collimator being measured are measured collimator line images, wherein the line images are stored in a machine-readable storage medium accessible to a processor unit;
   (f) said processor unit analyzing the reference collimator line images and the measured collimator line images and determining the offset distances dx, dy for each pair of lines between the reference collimator line images and the measured collimator line images; and
   (g) said processor unit calculating hole orientation angles θx, θy for each collimator hole in the collimator being measured, wherein the reference collimator line images and the measured collimator line images comprise line profile data representing radiation intensities detected by the detector and the step (f) comprising:
      (h) identifying and labeling all peaks in the line profile data of the reference collimator line images and the measured collimator line images, based on each peak's position relative to a center of the field of view of the detector;
      (i) calculating peak statistics for each peak;
      (j) determining whether each peak is a valid peak that satisfies a predetermined condition based on the peak statistics and the position of each peak;
      (k) re-labeling each valid peak based on the position of the valid peak relative to the center of the field of view of the detector; and
      (l) pairing the valid peaks from the line profile data of the reference collimator line images with the corresponding valid peaks from the line profile data of the measured collimator line images according to the re-labeled position of the valid peaks.

2. The method of claim 1, wherein the peak statistics includes a mean width and standard deviation of the peaks.

3. The method of claim 1, wherein the labeling of the peaks in step (h) comprises labeling the peaks using a set of integers $-L_x, -L_x+1, \ldots, -2, -1, 1, 2, \ldots, R_k-1, R_k$, where $R_k$ denotes the label of the right-most peak at kth scanning/stepping position, $-L_k$ denotes the label of the left-most peak at kth scanning/stepping position, and k runs from 1 to n, where n is the total number of scanning/stepping positions.

4. The method of claim 3, wherein the step (i) comprises finding the maximum common label L and the minimum common label R across all scanning/stepping positions and calculating the mean width $\mu_w$ and the standard deviation $\sigma_w$ for peaks with label L+1 or R-1.

5. The method of claim 4, wherein the predetermined condition in step (j) is satisfied for a given peak P=(x, w), where x is the peak position and w is the peak width, when conditions 1), $x>x_{min}+\alpha\mu_w$ and $x<x_{max}-\alpha\mu_w$, where $[x_{min}, x_{max}]$ is the detector's field of view interval and α is a predetermined threshold, and 2), $|w-\mu_w|<\beta\sigma_w$, where β is another predetermined threshold, are both satisfied.

6. A system for measuring a single photon emission computed tomography collimator's hole orientations comprising:
   a detector;
   a controllably movable stage;
   a plurality of parallel spaced line radiation sources positioned at a distance from the detector, wherein the plurality of line radiation sources are mounted on the controllably movable stage;
   a first collimator positioned between the detector and the plurality of line radiation sources;
   a control unit for controlling the movable stage, said control unit comprising: a machine-readable memory unit for storing a set of instructions for performing a method for measuring the single photon emission computed tomography collimator's hole orientations; and a processor unit for executing the set of instructions, wherein when said processor unit executes said set of instructions, the control unit performs said method comprising:
      (a) obtaining a set of line images of the plurality of line radiation sources by scanning/stepping the plurality of line radiation sources across the first collimator in a first direction;
      (b) obtaining a second set of line images of the plurality of line radiation sources by scanning/stepping the plurality of line radiation sources across the first collimator in a second direction that is orthogonal to the first direction;
      (c) repeating the steps (a) and (b) for a second collimator, wherein one of the two collimators is a reference collimator and the other of the two collimators is a collimator being measured, whereby the line images obtained using the reference collimator are reference collimator line images and the line images obtained using the collimator being measured are measured collimator line images, wherein the line images are stored in the machine-readable memory unit;
      (d) said processor unit analyzing the reference collimator line images and the measured collimator line images and determining the offset distances dx, dy for each pair of lines between the reference collimator line images and the measured collimator line images; and
      (e) said processor unit calculating hole orientation angles θx, θy for each collimator hole in the collimator being measured, wherein the reference collimator line images and the measured collimator line images comprise line profile data representing radiation intensities detected by the detector and the step (d) comprising:
   (f) identifying and labeling all peaks in the line profile data of the reference collimator line images and the measured collimator line images, based on each peak's position relative to a center of the field of view of the detector;
   (g) calculating peak statistics for each peak;
   (h) determining whether each peak is a valid peak that satisfies a predetermined condition based on the peak statistics and the position of each peak;

(i) re-labeling each valid peak based on the position of the valid peak relative to the center of the field of view of the detector; and (j) pairing the valid peaks from the line profile data of the reference collimator line images with the corresponding valid peaks from the line profile data of the measured collimator line images according to the re-labeled position of the valid peaks.

7. The system of claim 6, wherein the peak statistics includes a mean width and standard deviation of the peaks.

8. The system of claim 6, wherein the labeling of the peaks in step (f) comprises labeling the peaks using a set of integers $-L_x, -L_x+1, \ldots, -2, -1, 1, 2, \ldots, R_k-1, R_k$, where $R_k$ denotes the label of the right-most peak at kth scanning/stepping position, $-L_k$ denotes the label of the left-most peak at kth scanning/stepping position, and k runs from 1 to n, where n is the total number of scanning/stepping positions.

9. The system of claim 8, wherein the step (g) comprises finding the maximum common label L and the minimum common label R across all scanning/stepping positions and calculating the mean width $\mu_w$ and the standard deviation $\sigma_w$ for peaks with label L+1 or R−1.

10. The system of claim 9, wherein the predetermined condition in step (h) is satisfied for a given peak P=(x, w), where x is the peak position and w is the peak width, when conditions 1), $x>x_{min}+\alpha\mu_w$ and $x<x_{max}-\alpha\mu_w$, where [$x_{min}$, $x_{max}$] is the detector's field of view interval and $\alpha$ is a predetermined threshold, and 2), $|w-\mu_w|<\beta\sigma_w$, where $\beta$ is another predetermined threshold, are both satisfied.

* * * * *